United States Patent [19]
Spack et al.

[11] Patent Number: 5,750,356
[45] Date of Patent: May 12, 1998

[54] METHOD FOR MONITORING T CELL REACTIVITY

[75] Inventors: Edward G. Spack, Mountain View; Nancy G. Wehner, Fremont; Michael A. McCutcheon, Stanford, all of Calif.

[73] Assignee: Anergen, Inc., Redwood City, Calif.

[21] Appl. No.: 657,939

[22] Filed: May 31, 1996

[51] Int. Cl.$^6$ .................................................. G01N 33/53
[52] U.S. Cl. ........................................ 435/7.24; 435/7.94
[58] Field of Search ................................ 435/7.24, 7.94

[56] References Cited

U.S. PATENT DOCUMENTS

| | | | |
|---|---|---|---|
| 5,128,270 | 7/1992 | DeLacroix et al. | 435/7.24 |
| 5,334,504 | 8/1994 | Wood et al. | 435/7.24 |
| 5,344,755 | 9/1994 | Shearer et al. | 435/7.24 |

FOREIGN PATENT DOCUMENTS

WO 90/04182  4/1990  WIPO.

OTHER PUBLICATIONS

Cecil Czerkinsky et al., "Reverse ELISPOT Assay For Clonal Analysis of Cytokine Production, I. Enumeration of Gamma-Interferon-Secreting Cells," *The Journal of Immunological Methods*, vol. 110, 1988, pp. 29-36.

Tomas Olsson et al., "Autoreactive T Lymphocytes in Multiple Sclerosis Determined by Antigen-Induced Secretion of Interferon-γ," *J. Clin. Invest*, Rapid Publication, vol. 86, Aug. 1990, pp. 981-985.

Hans Link et al., "Myasthenia Gravis: T and B Cell Reactivities to the β-Bungarotoxin Binding Protein Presynaptic Membrane Receptor," *Journal of the Neurological Sciences*, vol. 109, 1992, pp. 173-181.

Söderström M. et al., "Optic Neuritis and Multiple Sclerosis: The T Cell Repertoires to Myelin Proteins and MBP Peptides Change With Time," *Acta Neurological Scandinavica*, 1994, vol. 90, pp. 10-18.

Söderström M. et al., "T Cells Recognizing Multiple Peptides of Myelin Basic Protein Are Found in Blood and Enriched in Cerebrospinal Fluid in Optic Neuritis and Multiple Sclerosis," *Scandinavica. J. Immunol.*, 1993, vol. 37, pp. 355-368.

Plebanski et al., "In vivo promary responses of human T cells to soluble protein antigens," *J. Immunol. Meth.* 1994, vol. 170, p. 12.

Sharrock et al., "Limiting dilution analysis of human T cells: a useful clinical tool," *Immunol. Today* 1990, vol. 11, pp. 281-286.

Weiner et al., "Double-blind pilot trial of oral tolerization with myelin antigens in multiple sclerosis," *Science*, 1993, vol. 259, p. 1321.

Manz et al., "Analysis and sorting of live cells according to secreted molecules, relocated to a call-surface affinity matrix," *Proc. Natl. Acad. Sci.* 1995, USA vol. 92, p. 1921.

Olsson et al., "Increased numbers of T cells recognizing multiple myelin basic protein epitopes in multiple sclerosis," *Eur. J. Immunol.*, 1992, vol. 22, pp. 1083-1087.

Sun, J-B et al., "T cells responses to human recombinant acetylcholine receptor-α subunit in myasthenia gravis and controls," *Eur. J. Immunol.* 1992, vol. 22, pp. 1553-1559.

(List continued on next page.)

*Primary Examiner*—David Saunders
*Attorney, Agent, or Firm*—Townsend and Townsend and Crew

[57] ABSTRACT

This invention provides a highly sensitive assay for the detection of T-cells reactive to an antigen by detecting a soluble factor whose secretion is induced by stimulation of the T-cell by the antigen. The assay includes an antigen-driven proliferation of specific T cells prior to restimulation with irradiated antigen presenting cells (APCs) and antigen. The assay can be performed on previously frozen PBMCs, providing greater convenience in sample processing, multiple use of a single sample as an internal standard, and simultaneous analysis of samples collected at different time points.

23 Claims, 4 Drawing Sheets

OTHER PUBLICATIONS

Link et al. "The T–cell repertoire in myasthenia gravis involves multiple cholinergic receptor epitopes," *Scand. J. Immunol.*, 1992, vol. 36, pp. 405–414.

Lu et al.. "Interferon μ–and interleukin–4–secreting cells in multiple sclerosis." *J. Neuroimmunol.*, 1993, vol. 46, pp. 123–128.

Lu et al "Interleukin–2 secreting cells in multiple sclerosis and controls," *J. Neurol. Sci.* 1993, vol. 120, pp. 99–106.

% POSITIVE RECALL ANTIGEN RESPONSES IN RHEUMATOID ARTHRITIS PATIENTS

| 3 DAY ASSAY | | 10 DAY ASSAY | |
|---|---|---|---|
| TT | PPD | TT | PPD |
| 15.4% | 7.7% | 50.0% | 71.4% |

% POSITIVE ANTIGEN RESPONSES IN MS PATIENTS

| | 3 DAY ASSAY | | 10 DAY ASSAY | |
|---|---|---|---|---|
| | MBP | MBP 84-102 | MBP | MBP 84-102 |
| ALL MS PATIENTS | 28.0 | 20.0 | 36.0 | 48.0 |
| DR2+ MS PATIENTS | 33.3 | 13.3 | 40.0 | 40.0 |

METHOD FOR MONITORING T CELL REACTIVITY

BACKGROUND OF THE INVENTION

1. Field of the Invention

This invention relates to detection of soluble factor secretion by activated T-cells. In particular, this invention relates to modifications of the ELISPOT assay.

2. Background of the Invention

Therapeutic strategies ranging from vaccine design to T cell specific immunosuppression require identification of immunodominant T cell epitopes and enumeration of T cell frequency. Several assays are currently employed to provide this information. Modified proliferation assays have been used to identify T cell epitopes based on stimulation indices of $\geq 2.0$ (Plebanski, M., and Burtles, S. S., *J. Immunol. Meth.* 170:15 (1994)), but this assay is extremely sensitive to variations in serum and often proves difficult for large scale clinical screenings. The limiting dilution assay (LDA) employs relatively large PBMC quantities and two rounds of in vitro stimulation to detect the T cell response to whole antigens or peptides (Sharrock, C. E. M. et al., *Immunol. Today* 11:281–286 (1990)). This assay has provided estimates of antigen specific CD4+ T cell frequencies ranging from approximately $1/10^3$–$1/10^5$ for alloreactive T cells (Sharrock supra) to $10^6$–$1/10^7$ for autoreactive T cells (Weiner, H. L. et al., *Science* 259:1321 (1993)). The LDA has been used to monitor efficacy in clinical trials, but the quantities of PBMC's (peripheral blood mononuclear cells) required limit the application of this assay in cases requiring frequent blood draws or the screening of large numbers of candidate peptides. Several flow cytometric methods can detect T cell activation by upregulation of characteristic markers such as CD69. Activation-induced T cell lymphokine production can be measured by flow cytometry using a monensin block of secretion, saponin permeabilization, and indirect immunofluorescent staining (Jung, T. et al., *J. Immunol. Meth.* 159:197 (1993)), or by trapping of secreted lymphokines on the surface of the secreting cell (Manz, R. et al., *Proc. Natl. Acad. Sci. USA* 92:1921 (1995)). These flow cytometry techniques are sufficiently sensitive when a relatively high frequency of T cells respond, as occurs in alloreactivity or superantigen stimulation, but they cannot detect most rare antigen-specific T cells. ELISA assays of lymphokine secretion are similarly limited to cases in which the responses of primed T cells, T cell clones, or high frequency T cells are measured. In situ hybridization of lymphokine mRNA is sufficiently sensitive to detect antigen-specific T cells with frequencies in the range of $1/10^4$–$1/10^5$ (Link, J. et al., *Neurol.* 44:728 (1994); Link, J. et al., *Ann. Neurol.* 35:197 (1994)), but this technique is not readily scalable to large sample numbers.

A modification of the ELISA assay (enzyme-linked immunosorbent assay), termed the immunospot or ELISPOT assay, has been developed to detect lymphokine secretion by individual T cells following antigen stimulation (Czerinsky, C., et al., *J. Immunol. Methods* 110:29–36 (1988); Olsson, T. et al., *J. Clin. Invest.* 86:981–985 (1990)). However, the sensitivity of the ELISPOT assay is low. In practice, for many patients, the standard ELISPOT assay of T cell responses to autoantigens can only be detected in cells sampled from the CSF, which entails difficult sampling and low cell yield. Identifying peptide epitopes within autoantigens such as MBP (myelin basic protein) by this assay is even more difficult given the relatively low precursor frequency. Furthermore, counting ELISPOT sample wells under light microscopy is slow and somewhat subjective. It would be desirable to have improved methods of measuring lymphokine secretion by activated T-cells, particularly those which occur at low frequency. This invention fulfils this and related needs.

SUMMARY OF THE INVENTION

One aspect of the invention provides a method for detecting an antigen reactive T-cell in a biological sample suspected of containing said T-cells. The method comprises:

(a) stimulating the T-cells in the biological sample with the antigen for a first time period sufficient to permit T-cell expansion;

(b) restimulating the T-cells with an effective amount of a combination of the antigen and antigen presenting cells to induce secretion of a soluble factor;

(c) detecting the presence of the soluble factor by capturing the soluble factor on a solid support; and (d) relating the presence of the soluble factor on the solid support to the presence of the antigen reactive T-cell.

Optionally, a second soluble factor such as, for example, a cytokine(s) and/or growth factor(s) may be added to facilitate continued T-cell expansion. This second soluble factor may be the same or different to the soluble factor whose detection is related to the presence of the antigen reactive T-cell.

The methods disclosed herein can be used to detect rare T-cells, especially those reactive to autoantigens and occurring at low frequencies, as low as 1 T-cell per $10^5$ PBMCs. A related aspect of the invention uses frozen T-cells as an internal control to validate the assay.

Also provided are methods for:

(1) identifying an antigen which stimulates T-cells in a patient biological sample (2) identifying a patient having T-cells reactive to an autoantigen, and (3) screening for putative drugs capable of inducing deletion or unresponsiveness of T-cells.

DESCRIPTION OF THE PREFERRED EMBODIMENTS

Figure 1:
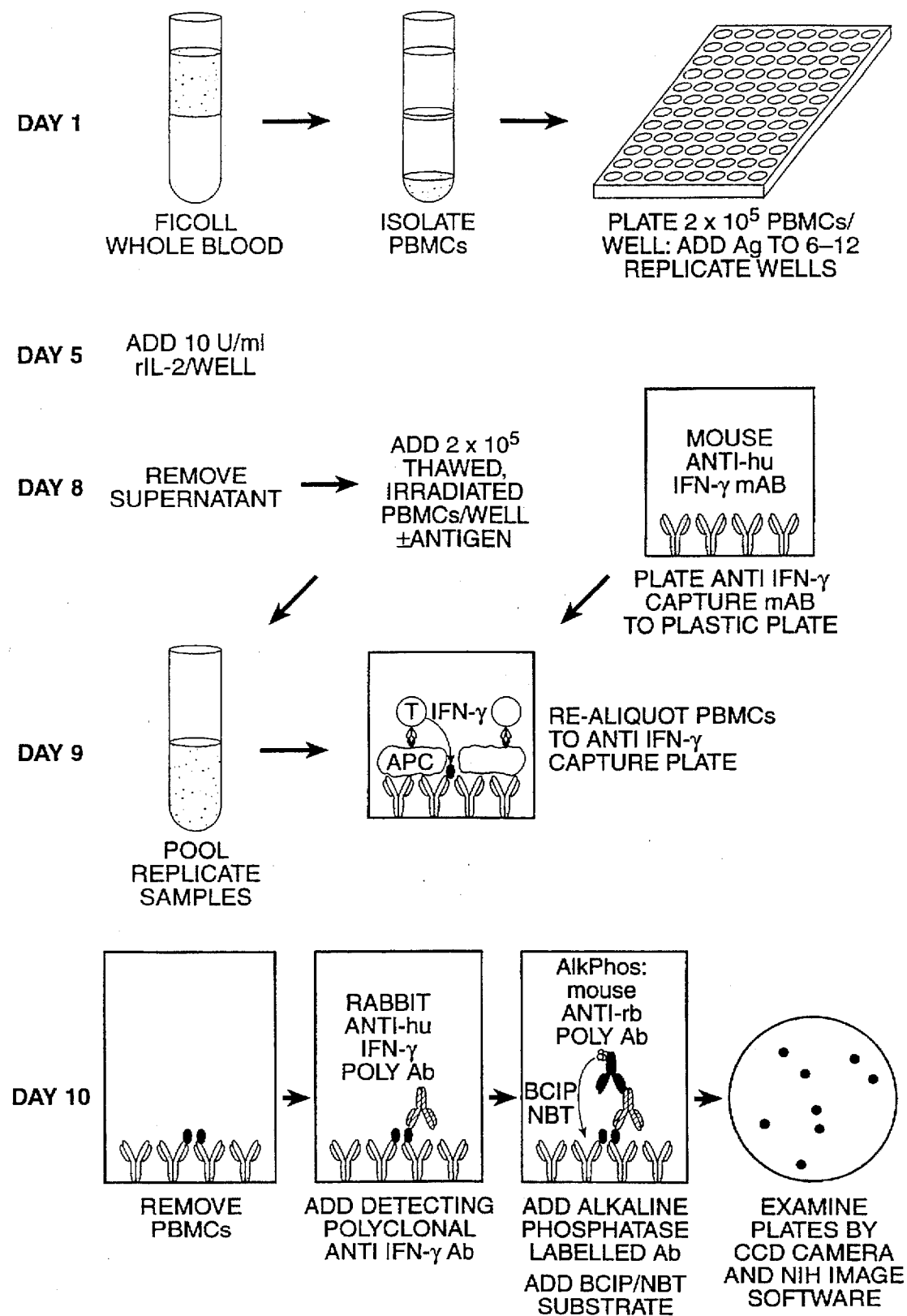
FIG. 1 shows a flow diagram of the 10 day ELISPOT assay.

This invention relates to the detection of T-cells reactive to an antigen by detecting a soluble factor whose secretion is induced by stimulation of the T-cell by the antigen. In one aspect, this invention relates to an ELISPOT assay which expands the proportion of antigen-responsive T cells before detection of secretion of the soluble factor, providing sufficient sensitivity to permit the screening of T cells which are present at low frequency. As a result, rare T-cells, such as those which are reactive to an autoantigenic peptide can be detected and monitored with a higher level of confidence than previously possible. The assay is typically performed as a solid phase ELISA which produces a signal from each responding T-cell, thus allowing T-cell enumeration. In one embodiment, the signal is produced in the form of a chromogen precipitate from an enzyme label, (a "spot", hence the term ELISPOT), and if desired, the spots are quantitated with a video camera linked to analysis software. The software can objectively subtract nonspecific chromogen precipitation from total signal and rapidly quantitate the number of spots. These modifications facilitate the use of the ELISPOT assay as a high volume screen for T cell responses in applications from including epitope identification, tracking of a patient's autoantigenic reactivity over time, and assessment of therapeutic efficacy in clinical trials.

One aspect of the invention modifies the standard ELISPOT assay of lymphokine secretion by single cells to increase the sensitivity of the method. As described herein, the invention provides for the detection of antigen reactive T-cells which secrete a variety of soluble factors. These modifications include:

(1) a 7 day amplification of antigen responsive T cells prior to detection of a soluble factor, (2) addition of a second soluble factor (e.g., a cytokine(s) and/or growth factor(s)) to facilitate continued T-cell expansion, (3) restimulation of the T-cells to secrete additional soluble factor by adding a second round of antigen in conjunction with antigen presenting cells, and (4) using previously frozen PBMCs as an internal control.

An assay of such T cell reactivity has several applications:

1. Early detection of autoimmune disease.
2. Identification of important autoantigenic peptides in a patient subpopulation (e.g. a particular HLA-DR allele) and in an entire patient population.
3. Selection of patients with given T-cell reactivity for participation in clinical trials.
4. Monitoring patient T cell reactivity during the course of chronic-progressive and relapsing-remitting diseases. The pattern of T cell reactivity might be useful in predicting the onset of disease relapse before clinical symptoms worsen, aiding in the titration of a therapeutic regimen.
5. Measuring the efficacy of a therapeutic regimen.

Thus, one aspect of the invention provides a method for detecting an antigen reactive T-cell in a biological sample suspected of containing said T-cells. The method comprises:

(a) stimulating the T-cells in the biological sample with the antigen for a time period sufficient to permit T-cell expansion, (b) restimulating the T-cells with an effective amount of a combination of the antigen and antigen presenting cells to induce secretion of a soluble factor, (c) detecting the presence of the soluble factor by capturing it on a solid support, and (d) relating the presence of the soluble factor to the presence of the T-cell.

Optionally, one may add a cytokine(s) and/or growth factor(s) to facilitate continued T-cell expansion during or after step (a).

The biological sample may be a biological fluid such as, but not limited to, whole blood, serum, plasma, nasal secretions, sputum, urine, sweat, saliva, transdermal exudates, pharyngeal exudates, bronchoalveolar lavage, tracheal aspirations, cerebrospinal fluid, synovial fluid, fluid from joints, vitreous fluid, vaginal or urethral secretions, or the like. Herein, disaggregated cellular tissues such as, for example, hair, skin, synovial tissue, tissue biopsies and nail scrapings are also considered as biological samples.

The assay is particularly useful for assaying T-cells in blood samples. Blood samples are usually processed to remove erythrocytes and platelets (e.g., by Ficoll density centrifugation or other such methods known to one of skill in the art) and the remaining PBMC sample, which includes the T-cells of interest, as well as B-cells, macrophages and dendritic cells, is used directly in the assay.

T cell lines require large quantities of blood, often as much as a unit. Collection of such large quantities is often unsafe for patients with autoimmune disease. The assay described herein uses $4 \times 10^5$ PBMCs per well, i.e. $2 \times 10^5$/ PBMCs for initial antigen stimulation and $2 \times 10^5$ irradiated PBMCs for restimulation. Therefore, several 15 ml blood collection tubes are generally sufficient for analysis of antigen reactivity with at least 6 wells per antigen.

The term "soluble factor" refers to proteins secreted by a T-cell in response to antigenic stimulation. A variety of secreted soluble factors can be detected by the assays disclosed herein. The soluble factors may be cytokines, lymphokines or chemokines. Typically this secreted factor is a lymphokine, such as enumerated below. As a result of the increased sensitivity of the assay, factors secreted by rare T-cells which occur in low frequency can be detected. Factors which are detected by this method include, but are not limited to lymphokines, cytokines and chemokines such as for example, IFN-$\gamma$, TNF-$\alpha$, IL-2, IL-3, IL-4, IL-10, IL-13 and GM-CSF. As one of skill in the art will recognize, any secreted factor which has two epitopes, each of which can be recognized by the specific binding pair members used in the subsequent sandwich assay detection step can be detected by this assay. This method finds particular utility in detecting rare T-cells, such as those which are reactive to an autoantigenic peptide.

The term "cytokine" refers to proteins made by cells that effect the behavior of other cells. Cytokines made by lymphocytes are generally termed "lymphokines" or interleukins (abbreviated IL). The term "chemokines" refers to a subset of cytokines with low molecular weight which effect the migration and activation of cells. Cytokines include interleukins (e.g., IL-2, IL-3, IL-4, IL-6, IL-10, IL-13 etc.,) macrophage arming factor, lymphocyte inhibition factor, macrophage inhibition factor, chemotactic factor, interferons, growth factors such as GM-CSF and the like.

The time period for T-cell expansion is typically greater than 3 days. Depending on the rapidity with which results are needed and the assay sensitivity required, this time period could be 5–7 days or as high as 10–14 days. With such long expansion phases it is generally advantageous to add a cytokine and/or growth factor at an intermediate point during the expansion phase to facilitate continued T-cell expansion and prevent premature cell death due to apoptosis.

The choice of cytokine and/or growth factor which is added to the assay medium to facilitate continued T-cell expansion is controlled partly by the subset of T-cells being detected. For example, IL-2 upregulates expression of the IL-2 receptor and supports the expansion of $T_h1$ cells, whereas IL-4 supports the expansion of $T_h2$ cells. In other cases, combinations of one or more cytokines and/or growth factors can be used.

In this modification of the ELISPOT assay, the number of progeny cells from a single precursor T-cell and consequently the amount of soluble factor-secreting cells increases. This leads to an increased number of "spots" on the solid surface being used and thus provides a greater assay response. Such an increased assay response is more amenable to statistical sampling and provides higher signal to background ratios, lower standard deviations and higher confidence levels. As a result, T-cells with expected frequencies in the range of 1 per $10^5$ PBMCs in the biological sample are detectable, frequently as low as 5 per $10^6$ PBMC's, often as low as 1 per $10^6$ PBMCs. Similar advantages accrue when a detection method other than an ELISPOT assay is used.

"Specific binding pair member" (sbp member) shall mean a molecule which is one of two different molecules, having an area on the surface or in a cavity which specifically binds to and is thereby defined as being complementary with a particular spatial and polar organization of the other molecule. The two molecules are related in the sense that their binding to each other is such that they are capable of distinguishing their binding partner from other assay constituents having similar characteristics. The members of the specific binding pair are referred to as ligand and receptor (antiligand), sbp member and sbp partner, and the like. Complementary sbp members bind to each other, as for example, a ligand and its complementary receptor. Sbp members will usually be members of an immunological binding pair such as an antigen-antibody, although other specific binding pairs, such as biotin-avidin, hormones-hormone receptors, nucleic acid duplexes, IgG-protein A, and the like are specific binding pairs which are not immunological binding pairs. In the context of this invention, specific immunological binding pairs include, but are not limited to, antibodies against secreted soluble factors, such as the lymphokines, cytokines and chemokines enumerated above, particularly anti-human antibodies and antibodies against specific epitopes of these secreted factors.

"Antibody" shall mean an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof, which immunoglobulins include the various classes and isotypes, such as IgA (IgA1 and IgA2), IgD, IgE, IgM, and IgG (IgG1, IgG2, IgG3, and IgG4) etc. Fragments thereof may include Fab, Fv and F(ab')$_2$, Fab', and the like.

It is typically advantageous to perform the stimulation/expansion phase described above on multiple duplicate samples and then pool the expanded samples prior to detection. This is particularly useful when assaying for rare T-cells of which only a few, e.g., as low as 1–2 T-cells/$10^5$ cells, sometimes as low as 5 T-cells/$10^6$ cells, may be present in the original sample. Pooling the samples before the detection step reduces sample to sample variation and increases the statistical confidence levels of the assay. Typically, the assay is run in triplicate or sextuplicate prior to pooling, though a different level of duplication can also be employed.

A variety of assay formats can be used to detect the increased levels of secreted factors produced by the assay described herein. Suitable assays include both solid phase (heterogeneous) and non-solid phase (homogeneous) protocols. The assays can be run using competitive or non-competitive formats, and using a wide variety of labels, such as radioisotopes, enzymes, fluorescers, chemiluminescers, spin labels, and the like. Such methods include, but are not limited to enzyme-linked immunosorbent assays (ELISA), both direct and reverse formats, and other solid phase assays. It will be recognized that negative controls, i.e., samples run without added antigen, and positive controls, i.e., samples run with antigens, such as tetanus toxoid, known to elicit lymphokine secretion from T-cells will be run as necessary under otherwise duplicative conditions to validate the assay results.

Some assays rely on heterogeneous protocols where a ligand complementary to the secreted factor (such as antibody against the secreted factor) is bound to a solid phase which is used to capture the secreted factor. The ligand may be conveniently immobilized on a variety of solid phases, such as dipsticks, particulates, microspheres, magnetic particles, test tubes, microtiter wells, and plastics, nitrocellulose or nylon membranes and the like. The captured factor can then be detected using the non-competitive "sandwich" technique where a directly or indirectly labelled second ligand for the factor is exposed to the washed solid phase. Such assay techniques are well known and well described in both the patent and scientific literature. See, e.g., U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Enzyme-linked immunosorbent assay (ELISA) methods are described in detail in U.S. Pat. Nos. 3,791,932; 3,839,153; 3,850,752; 3,879,262; and 4,034,074. ELISA assays detect very low titers of secreted factors. Also see, "Enzyme immunohistochemistry" in *Practice and theory of enzyme immunoassays*, P. Tijssen (Elsevier 1985).

A commonly used assay format is the antibody capture assay. The general protocol is simple: a ligand, e.g., an unlabelled antibody for the secreted factor, is immobilized on a solid phase, and the secreted factor is allowed to bind to the immobilized antibody. The bound secreted factor is then detected by using a labelled secondary reagent that will specifically bind to the captured factor ("direct sandwich assay"). Alternatively, the secondary reagent will not be labelled, but will be detected by subsequent binding to labelled tertiary binding reagent complementary to the second binding reagent ("indirect sandwich assay"). The strength of signal from the bound label allows the determination of the amount of secreted factor present in the sample and this in turn allows the quantitation of the number of activated T-cells present in the sample.

A variety of labelled secondary and/or tertiary reagents can be used to detect the presence of the bound secreted factor. Examples include, but are not limited to, anti-cytokine antibodies, anti-immunoglobulin antibodies, peroxidase/anti-peroxidase avidin/biotin complexes, protein A and protein G.

Detectable labels suitable for use in the present invention include any composition detectable by photochemical, biochemical, immunochemical, electrical, optical or chemical means. Useful labels in the present invention include biotin for staining with labeled streptavidin conjugate, fluorescent dyes and/or substrates (e.g., fluorescein, texas red, rhodamine, green fluorescent protein, ELF™ (Molecular Probes, Eugene, OR, catalog #E-6600) and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), colorimetric labels such as colloidal gold or colored glass or plastic (e.g., polystyrene, polypropylene, latex, etc.) beads and chemiluminscent labels. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent or chemiluminescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. Labels which are particularly useful in an ELISPOT assay as described herein are those which can produce a particulate product, such as when the combination of an enzyme and a substrate which gives a precipitating product. Combinations of such enzyme substrate pairs are alkaline phosphatase and 4-bromo-3-chloro indolyl phosphate/tetrazolium salts, naphthol AS-MX or napthol AS phosphate/Fast Blue BBN or Fast Red TR; horse radish peroxidase and 4-chloro-1-naphthol, 3,3'-diaminobenzidine (DAB), p-phenylenediamine, 3-amino-9-ethylcarbazole (AEC), 5,5'-tetramethylbenzidine and the like; glucose oxidase and t-nitroblue tetrazolium chloride (t-NBT)/m-phenazine methosulfate.

In another aspect of the invention, a second round of stimulation is performed. Frequently, assays which are run with pooled samples as described above, and a second round of stimulation is done on the pooled samples. In one embodiment, this second round of stimulation is done with the patient's own cells. A portion of the patient sample is separately preserved, typically by freezing at the onset of the assay, often as low as at liquid nitrogen temperatures, and a remaining portion is expanded and pooled as described above. The preserved portion is thawed, treated by irradiation, chemical treatment (e.g. mitomycin C) or the like to block proliferative capacity and added to the expanded samples in conjunction with another round of antigen. This procedure serves to stimulate the T-cells with a second round of antigen presenting cells and the irradiation ensures that the added cells do not expand independently. Typically, this second round of stimulation is done for 1-3 days, preferably 1 day.

The antigen presenting cells used in this second round of stimulation may also come from a source other than the original patient, as long as one avoids a mismatching at some of the MHC class I or class II alleles which could result in a mixed lymphocyte reaction and unacceptably high background in the zero antigen negative control wells. For example, one can use lymphocyte cells transfected with the appropriate MHC II molecule involved in peptide binding and T-cell recognition. One may also use EBV (Epstein Barr Virus) transformed B-cells, either a homozygous cell line available commercially which matches the patient's MHC haplotype or a previously prepared EBV transformed B-cell line from the patient. Finally, one may perform this second round of stimulation with a MHC II-antigen complex which is immobilized on the surface of the well.

The methods disclosed herein can be used to detect T-cells reactive to a variety of antigens, including the autoantigens which are indicative of an autoimmune disease. Table 1 enumerates a representative and non-limiting selection of disease states and their implicated autoantigens.

TABLE 1

| DISEASE | KNOWN OR SUSPECTED AUTOANTIGENS |
| --- | --- |
| Multiple Sclerosis (MS) | myelin basic protein (MBP) proteolipid protein (PLP) major oligodendrocytic protein (MOG) myelin associated glycoprotein (MAG) αB- crystallin |
| Myasthenia Gravis (MG) | acetylcholine receptor (AChR) |
| Insulin Dependent Diabetes Mellitus (IDDM) | glutamic acid decarboxylase (GAD) insulin |
| Uveitis | S protein |
| Rheumatoid Arthritis (RA) | collagen heat shock proteins (HSPs) e.g. hsp65 aggrecans proteoglycans fillagrin link |
| Psoriasis | desmin |
| Pemphigus Vulgaris | epiderimal cadherin |
| Inflammatory Bowel Disease (IBD) | tropomyosin |
| Systemic Lupus Erythematosus (SLE) | Sm, RNP histones |
| Graves Disease | thyroid stimulating hormone receptor |
| Hashimoto's Thyroiditis | thyroglobulin thyroid peroxidase |
| Goodpasture's Syndrome | collagen type IV |
| Autoimmune Thrombocytopenia Purpura | platelet integrin gp11b:111a |
| Autoimmune Hemolytic Anemia | Rh blood group 1 antigen |

Myelin basic protein and peptide components thereof are indicative of multiple sclerosis. Particular autoantigenic peptides which can be used in this assay are MBP 83–102 (this refers to the peptide composed of residues 83–102 of MBP) and MBP 144–163, the major oligodendrocyte glycoprotein peptides MOG 1–20 and MOG 41–60, and the proteolipid protein peptides PLP 40–60, PLP 89–106, PLP 105–124, PLP 30–49, PLP 95–116, and PLP 180–199.

Another aspect of the invention is a method of periodically monitoring levels of antigen reactive T-cells in a patient. This allows one to track the progression or amelioration of disease in a patient and also to track the efficacy of a therapeutic regimen. The method comprises:

(a) providing a sample of PBMCs from the patient;

(b) freezing a portion of the sample of PBMCs to provide a control sample;

(c) assaying the level of antigen reactive T-cells in the patient at periodic intervals using the assays described above;

(d) assaying the level of antigen reactive T-cells in a freshly thawed portion of the control sample using the assays described above; and (e) comparing the levels observed in (c) and (d) to monitor the levels of antigen reactive T-cells in the patient.

As described in more detail in the Examples, the present invention has demonstrated that T-cells preserved, typically by freezing, can be thawed and assayed using the methods described herein without affecting the viability of the cells or the accuracy of the subsequent T-cell enumeration. Using these preserved T-cells as an ongoing control provides a baseline against which temporal fluctuations in a patient's T-cell level can be compared. Therefore, any observed variation in a patient's T-cell count can be normalized against this control and the residual variation, if any, can be attributed to the progression or amelioration of a particular disease state being monitored. Such studies can use T-cells which have been preserved for as long as six months, often as long as 1–2 years. An advantage of having such an external standard which provides a stable snapshot of the patient's initial condition is that low level variations in the assay can be attributed to an actual change in the patient condition. Apart from being an objective measure of the disease state, it also allows one to detect a change in disease state before more dramatic clinical symptoms appear.

The methods disclosed herein are also used to determine which patients react to a suspected or known autoantigen. This is useful for selecting patients for clinical trials in which one desires to test the efficacy of a particular drug for a disease state caused by a suspected or known autoantigen. It can also help determine the DR, DP or DQ restriction of this response by using blocking antibodies or transfected L cells as the antigen presenting cells.

Also provided are methods of determining/confirming whether an antigen, typically a protein or component thereof, is an autoantigen in a significant portion of a patient population. In some diseases, e.g., rheumatoid arthritis, there is no acknowledged dominant autoantigenic protein and the assays described herein can be used to compare T-cell responses of a patient sample to various whole proteins derived from inflamed joints. In other diseases, such as myasthenia gravis or multiple sclerosis, the autoantigen responsible for the disease is known or suspected, but the immunodominant portion(s) of the autoantigenic proteins which dominate the T-cell response are not known. In such situations, PBMCs can be stimulated with various peptides derived from the autoantigen, either using a complete set of overlapping peptides or a subset of only those peptides which bind strongly to the relevant MHC II allele. Alternatively, PBMCs can be stimulated with the entire autoantigen in the initial round of stimulation, and restimulated with suspected autoantigenic peptides. Such peptides can be prepared by solid phase peptide synthesis methods when their sequences are known or peptide fragments can be prepared from the autoantigen by chemical or enzymatic digestion, all methods known to one of skill in the art.

EXPERIMENTAL

Antigens

The following antigens were tested for their ability to induce IFN-γ secretion by PBMCs: tetanus toxoid (TT) (List Biologicals #191B, Campbell, Calif.), tuberculin purified protein derivative from *Mycobacterium tuberculosis* (PPD) (Connaught #SP0008, Swiftwater, Pa.), and human myelin basic protein (hMBP) (Chemicon International, Inc. #AG42P, Temecula, Calif.). Peptides including the immunodominant peptides MBP 84–102 and MBP 143–168 were synthesized using F-MOC chemistry and checked for purity by HPLC and mass spectroscopy.

EXPERIMENT I

Measurement of Antigen Reactive T-Cells

A summary flow chart of the method is shown in FIG. 1. In brief, peripheral blood is diluted threefold in Dulbecco's phosphate buffered saline (DPBS), underlain with 15 ml of Ficoll (Pharmacia Ficoll-Paque #17-0840-02, Piscataway, N.J.) per 40 ml diluted blood in a 50 ml polypropylene centrifuge tube, and spun at 2000 RPM for 20 minutes in a Beckman CS-6R centrifuge (Beckman Inc., Palo Alto, Calif.). The buffy layer at the DPBS/Ficoll interface is removed, washed twice with DPBS and once with human tissue culture medium (hTCM: αMEM+5% heat inactivated human AB serum (Ultraserum, BioWhittaker, Walkersville, Md.), penicillin/streptomycin, 1-glutamine) at low RCF to remove platelets. Sixty percent of the PBMCs are resuspended in freezing medium (10% dimethyl sulfoxide(Sigma Chenical Co., St. Louis, Mo.), 90% fetal bovine serum to a concentration of $5 \times 10^6$ cells/ml, frozen in a programmable Cryo-Med (New Baltimore, Mich.) cell freezer, and stored under liquid nitrogen until needed.

The purified PBMCs are plated at $2 \times 10^5$ cells/well at a volume of 0.1 ml in 96 well Costar cell culture plates. An equal volume of antigen at 10 μg/ml is added to triplicate or sextuplet sets of wells and the plate is incubated in a 37° C., 5% $CO_2$ incubator. On day five, 10 μl/well of 100 U/ml stock recombinant IL-2 (Advanced Biotechnologies Inc., Columbia, Md.) is added to each well. On day 8, frozen PBMCs are thawed, washed in DPBS+0.5% bovine serum albumin (BSA) to remove DMSO, resuspended to a concentration of $4 \times 10^6$ cells/ml in hTCM, and γ-irradiated (3,000 RADS). Fifty microliters/well are dispensed along with 50 μl of the appropriate antigen at a stock concentration of 40 μl/ml to give a final antigen concentration of 10 μg/ml.

To prepare a capture plate, IFN-γ capture antibody (monoclonal mouse anti-human IFN-g, Endogen #M700A, Cambridge, Mass.) is diluted to 10 μg/ml in sterile 0.1 M $Na(CO_3)_2$ pH 8.2 buffer, aliquotted at 50 μl/well in flat bottomed 96 well sterile microtiter plates (Corning Costar Corp.), and incubated at 4° C. for a minimum of 24 hours. Prior to use, excess antibody is removed and wells are washed twice with dPBS+1% Tween 20 (PBST). To block further nonspecific protein binding, plates are incubated with 250 μl/well of PBS+5% BSA at room temperature for 1 hour. After discarding the blocking solution, wells are washed once with PBST (0.1% Tween), followed by hTCM in preparation for the antigen stimulated cells.

On day 9 of the assay, twenty four hours after the second antigen stimulation, the stimulation plate is spun for 5 minutes at 1500 RPM in a Beckman CS-6R centrifuge and 90 μl of supernatant is carefully removed from each well with a micropipette. The pelleted cells are resuspended in 100 μl of hTCM, pooled in sterile tubes (Corning Costar corp sterile ClusterTAb #4411, Cambridge, Mass.), mixed and transferred into an equal number of wells of an anti IFN-γ capture plate. Capture plates are incubated undisturbed at 37° C. for 16–20 hours. At the end of the IFN-γ secretion phase, the cells are discarded and the plates are washed three times with 0.1% PBST. A final aliquot of PBST is added to the wells for ten minutes, removed, and 100 μl of a 1:500 dilution of rabbit anti-human IFN-γ polyclonal antibody (Endogen #P700, Cambridge, Mass.) in PBST+1% BSA is added to each well for 3.5 hours at room temperature with gentle rocking. Unbound anti-IFN-γ polyclonal antibody is removed by three washes with PBST, followed by a wash with 250 μl of 1X Tris-buffered saline+0.05% Tween 20 (TBST). Next, a 100 μl aliquot of 1:5000 alkaline phosphatase-conjugated mouse anti-rabbit polyclonal antibody (Jackson Immunological #211-055-109, West Grove, Pa.) diluted in TBST is added to each well and incubated at room temperature for 1.5–2 hours with gentle rocking. Excess enzyme-conjugated antibody is removed by three washes with PBST and two washes with alkaline phosphatase buffer (APB=0.1 M NaCl, 0.05 M $MgCl_2$, 0.1 M Tris HCl, pH 9.5) followed by addition of the substrate mix of p-Toluidine salt and nitroblue tetrazolium chloride (BCIP/NBT, GIBCO BRL #18280-016, Gaithersburg, Md.). To stop the calorimetric reaction, plates were washed three times in $dH_2O$, inverted to minimize deposition of dust in the wells, and dried overnight at 28° C. in a dust free drying oven.

Images of the spots corresponding to the lymphokine secreted by individual antigen-stimulated T cells are captured with a CCD video camera and the image is analyzed by NIH image software. Captured images are enhanced using the Look Up Table which contrasts the images. Thresholding is then applied to every image and a wand tool is used to highlight the border to effectively subtract the edge of the well so that background counts won't be high and artificial. Density slicing over a narrow range is then used to highlight the spots produced from secreting cells. Pixel limits are set to subtract out small debris and large particles, and the number of spots falling within the prescribed pixel range are counted by the software program. Totals from each well are then manually recorded for future analysis. Alternatively, spots can be counted by other commercially available or customized software applications, or may be quantitated manually by a technician using standard light microscopy. Spots can also be counted manually under a light microscope.

The protocol detailed above specifies conditions for the enumeration of single IFN-γ secreting T cells. Substituting appropriate capture and detection antibody pairs permits the application of this assay to the detection of T cells secreting other soluble factors. A partial list of antibody pairs which can be used in this assay is presented in Table 2.

TABLE 2

LYMPHOKINE ELISPOTS

| LYMPHOKINE | CAPTURE ANTIBODY | DETECTION ANTIBODY |
|---|---|---|
| hIFN-γ | mouse anti-hIFN-γ mAb (Endogen M700A, Cambridge, MA) | rabbit anti-hIFN-γ poly Ab (Endogen P700, Cambridge, MA) hTNF-α mouse anti-hTNF-α mAb (R&D Systems #270, Minneapolis, MN) goat anti-hTNF-α poly Ab (R&D Systems #210 NA, Minneapolis, MN) |
| hIL-2 | mouse anti-hIL-2 mAb (R&D Systems #202, Minneapolis, MN) | goat anti-hIL-2 poly Ab (R&D systems #202 NA, Minneapolis, MN) |
| mIFN-γ | rat anti-mIFN-γ mAb (Pharmingen 18181D, San Diego, CA) | bt-rat anti-mIFN-γ poly Ab (Pharmingen 18112D, San Diego, CA) |

Figure 2:
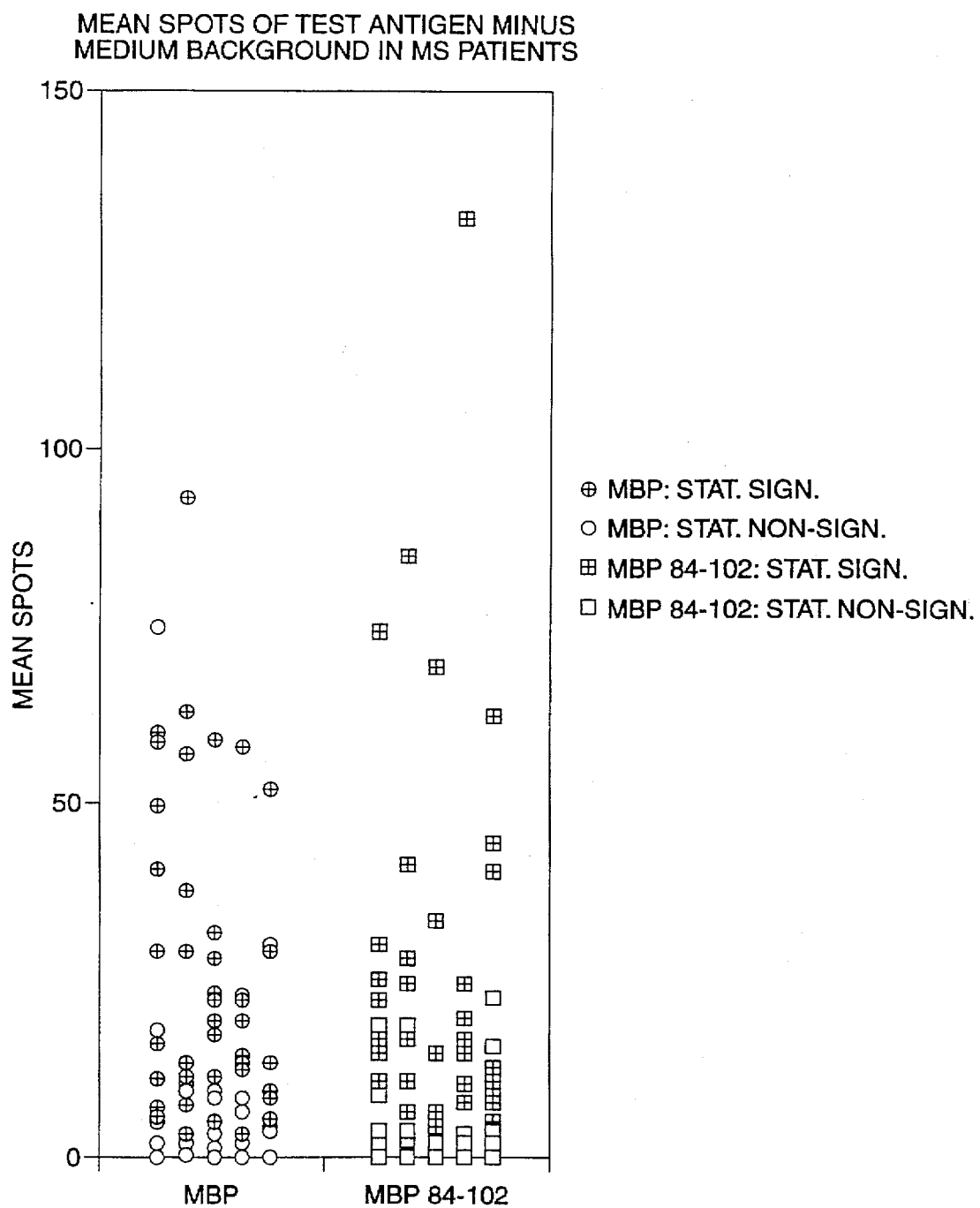
FIG. 2 shows MBP and MBP 84–102 reactivity in PBMCs from MS patients.

FIG. 2 shows measurements of the reactivity of MS patients and healthy donors to MBP and MBP 84–102 using the above described assay.

The reproducibility of this assay was demonstrated by performing the assay on frozen PBMCs from the same donor over the course of 11 weeks with different technicians performing the assay. Performing the stimulation phases of the assay on plastic round bottom wells gave superior results. Application of this assay to the screening of a patient population for reactivity to an autoantigen has also been demonstrated.

EXPERIMENT II

Comparison of 3 and 10 Day ELISPOT Formats

An ELISPOT assay was developed to identify patients with reactivity to the immunodominant peptide MBP 84–102. This assay is used for two phases of an MS clinical trial, patient recruitment and monitoring of the T cell response during the trial. The ELISPOT assay cited in the literature measures the lymphokine response of PBMCs immediately following antigen stimulation, a 3 day assay from blood draw to plate reading. This format is sufficient for the detection of relatively frequent T cells such as alloreactive- or TT-reactive T cells. However, for rare T cells such as autoreactive cells, the average patient has only 1–3 lymphokine producing cells/$10^5$ PBMCs in a 3 day ELISPOT. This level of response is too low for good statistical analysis. In the assay method of this invention, PBMCs were expanded for a 10 day period, and subjected to a round of antigenic stimulation prior to lymphokine assay so that there would be more responding cells to measure. In this 10 day format, PBMCs were stimulated with antigen on day 0, given IL-2 on day 5, and restimulated on day 8 before transfer to the antibody capture plate on day 9 and chromagen development on day 10. The increased sensitivity afforded by this T cell expansion prior to detection of lymphokine secreted by individual cells is shown below.

Figures 3, 4:
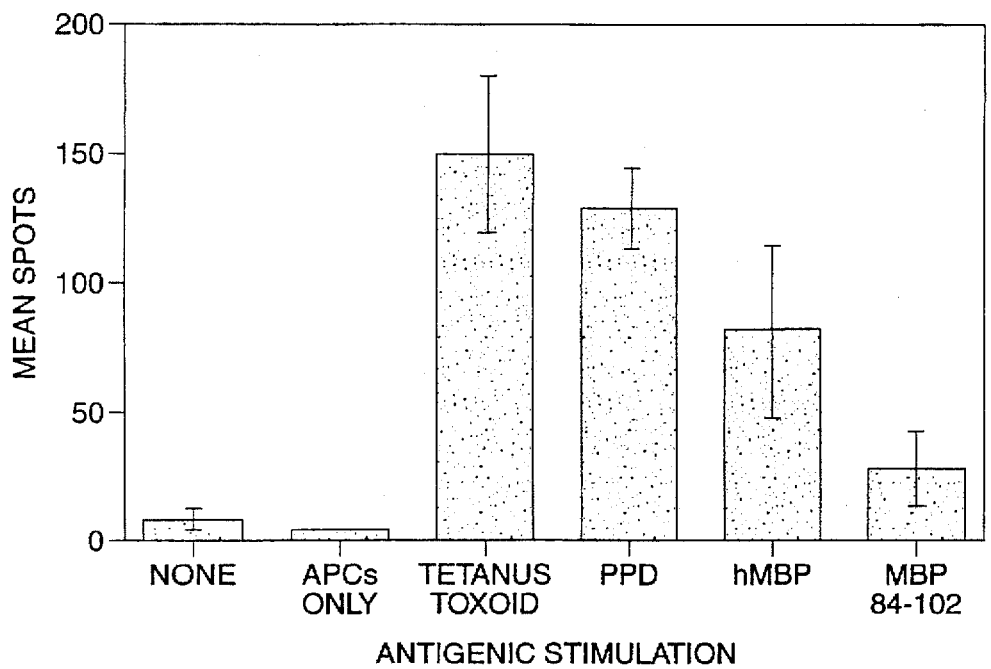
FIG. 3 shows IFN-γ produced by multiple sclerosis PBMCs following secondary stimulation by selected antigens
FIG. 4 shows comparison of IFN-γ spots obtained in the 3 day and 10 day assay formats. Antigens: TT, PPD, autoantigen (MBP, MBP 84–102).

In the standard ELISPOT assay reported in the literature, PBMCs are mixed with antigen in a capture plate containing anti-lymphokine antibody for 1–2 days followed by detection with an enzyme-linked second antibody (3 day format). This assay tests $2 \times 10^5$ PBMCs per well, and because the frequency of autoreactive T cells in peripheral blood is on average in the range of 1–5/$10^5$ there are very few specific cells per well that can respond in the average patient. To increase the number of responders, the PBMCs were subjected to a round of ex vivo antigen stimulation prior to testing the recall response by lymphokine secretion. In other words, PBMCs were incubated with antigen or medium for 8 days, washed, restimulated with fresh irradiated APCs and antigen, and these restimulated cells were tested for secretion of IFN-γ by the capture ELISPOT (10 day format). Pooling all of the expanded cells from sextuplet wells and realiquoting them on day 9 into the capture plate improves the standard deviations. Table 3 shows an early comparison of the two assay formats with blood from the same patient. The day 3 format gives a very low background, and the response to TT is measurable, averaging 36.7±15.3 IFN-γ spots for patient MS.M027. However, the response to whole human MBP and to the immunodominant peptide MBP 84–102 was nearly background and too low for effective statistical analysis. In contrast, a 7 day expansion before assay of lymphokine secretion yielded a higher background (25.0±1.4) but also a measurable improvement in the response to hMBP and to MBP 84–102. The response to TT was also increased in the 10 day format, with an average of nearly 100 spots per well. This density of response approaches the resolution limits of the video camera and software, reflecting the higher frequency of TT-reactive T cells in peripheral blood. For many patients and healthy controls the response to TT and/or to PPD is off scale in this 10 day format, and we are experimenting with starting dilutions which will keep the 10 day recall response to this antigens within measurable limits. As can be seen in FIGS. 3 and 4, many patients now give strong responses to hMBP and/or MBP 84–102, as well as recall antigens such as TT and PPD, which can be compared with medium controls by Mann-Whitney analysis.

TABLE 3

Sample MS patient responses to antigens and medium in the 3 day and 10 day ELISPOT assay formats

| PATIENT | FORMAT | MEDIUM | TT | hMBP | MBP 84-102 |
|---|---|---|---|---|---|
| MS.M027 | 3 d assay | 0 ± 0 | 37 ± 15 | 1 ± 1 | 1 ± 1 |
| | 10 d assay | 25 ± 1 | 99 ± 19 | 56 ± 31 | 63 ± 16 |
| MS.F134 | 10 d assay | 17 ± 3 | | 36 ± 5 | 27 ± 7 |

EXAMPLE III
Comparison of Fresh vs. Frozen PBMCs in a 10 Day ELISPOT Assay

Objectives:

The objective of these experiments was to determine if reactivity to antigens was comparable and consistent between fresh PBMCs isolated from MS patient whole blood and frozen cells from the same patient. If so, frozen cells could provide an internal control with future bleeds from patients during clinical trials. The assay was done as described above using on day 1 either fresh PBMCs or frozen PBMCs which were thawed before use in the assay.

Results:

Three experiments looked at patient and in-house frozen PBMCs performance in the assay using two different MS patients, MS.F165 and MS.M122, and several in-house donors. The first experiment was run using patient frozen cells to see if indeed we could get reactivity. In the second experiment, 7 in-house donors were run with fresh and frozen cells for comparison. The third experiment involved multiple runs of frozen cells from an in-house donor over time. The results (Tables 4,5–6, FIGS. 4,6) showed that frozen PBMC's can be used in a complete ELISPOT assay and produce positive results in the form of spots.

In the first experiment, it can be seen from the two runs with MS patients (Tables 4,5) that, in addition to a positive TT response, an MBP response is present.

TABLE 4

Results of frozen experiment with patient MS.F165. Numbers represent mean spots from plate counted using NIH Image.

| Frozen PBMC's | Media | Tet. Tox. | whle. hMBP | MBP84-102 |
|---|---|---|---|---|
| Mean | 6 | 65 | 16 | 7 |
| Std. Dev. | 2 | 12 | 3 | 4 |

TABLE 5

Results of fresh vs. frozen experiment with patient MS.M122. Numbers represent mean spots from plate counted using NIH Image 1.58.

| PBMC's | Media | Tet. Tox. | whle. hMBP | MBP84-102 |
|---|---|---|---|---|
| Fresh | 44 | 69 | 31 | 40 |
| Std. Dev. | 29 | 19 | 10 | 20 |
| Frozen | 10 | 120 | 45 | 33 |
| Std. Dev. | 5 | 23 | 21 | 10 |

Figure 5:
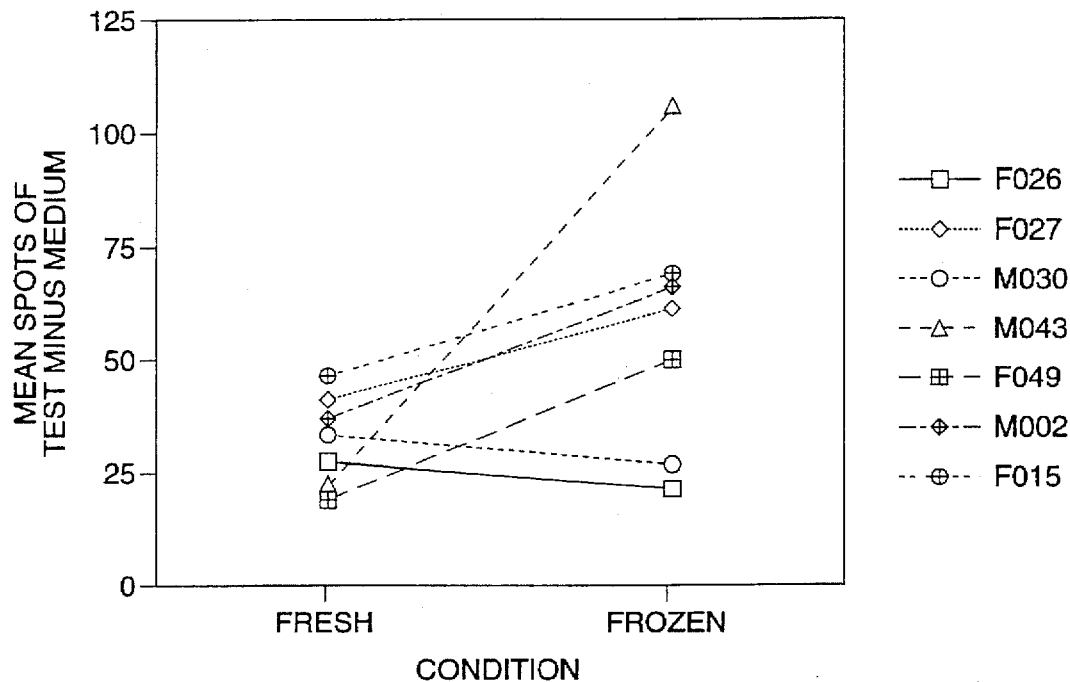
FIG. 5 shows the comparison between two experiments done on freshly isolated and frozen PBMCs thawed and then run on a 10 day ELISPOT assay. The cells are derived from healthy donors.

In the second experiment, shown in FIG. 5, in-house healthy donors were evaluated for their TT response in the assay. Statistically significant responses to TT were found in all 7 donors. Responses from frozen cells were equivalent to or better than those obtained from fresh cells. This improved background to signal ratio was also seen in MS.M122 (Table 5) and its cause is currently under investigation.

Figure 6:
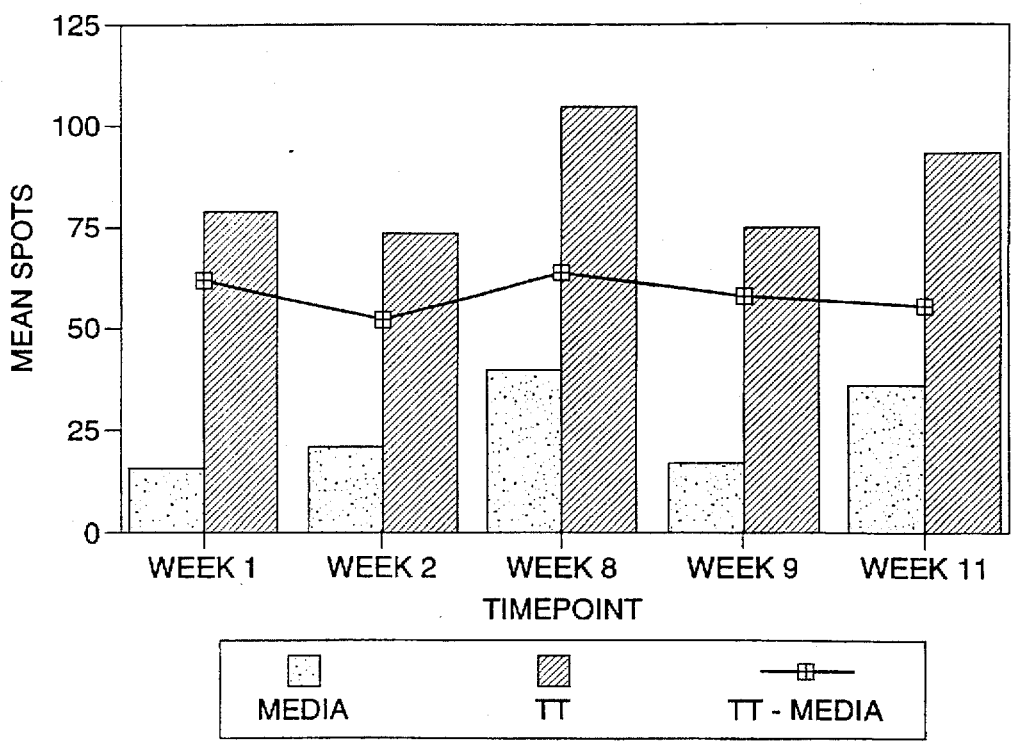
FIG. 6 shows the use of frozen PBMCs as a source of T cells and its utility as a reproducible internal control for the assay.

The third experiment looked at the response of the frozen cells of a known TT positive in-house donor, AN.M036. Frozen cells were derived from a unit of donated blood which was processed and frozen on the day of the unit draw collection. Aliquots of the cells were thawed at various time intervals and run in the assay as described above. Timepoints shown were done by three different technicians. FIG. 6 shows the stability/reproducibility of the response over an 11 week period. This stability/reproducibility allows for the use of such cells as an internal control for the assay.

Conclusions

In conclusion, it can be seen that the use of frozen peripheral blood mononuclear cells in a ten day ELISPOT assay works in a consistent manner. The results of the experiments are presented in graph form in FIGS. 5 and 6 and demonstrate that frozen PBMCs from a good responder to Tetanus Toxoid can be used as a positive control in clinical trials.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A method for detecting an antigen reactive T-cell in a biological sample suspected of containing said T-cells, the method comprising:
    (a) stimulating the T-cells in the biological sample with said antigen for a first time period sufficient to permit T-cell expansion;
    (b) restimulating the T-cells with an effective amount of a combination of the antigen and antigen presenting cells for a second time period effective to induce secretion of a soluble factor;
    (c) detecting the presence of the soluble factor by capturing the soluble factor on a solid support; and
    (d) relating the presence of the soluble factor on the solid support to the presence of the antigen reactive T-cell.

2. The method of claim 1, wherein the time period in step (a) is at least four days.

3. The method of claim 1, wherein the biological sample is blood.

4. The method of claim 1, wherein the combination of antigen and antigen presenting cells of step (b) is prepared by:
    (1) separately preserving a portion of the biological sample by freezing;
    (2) thawing the portion of the biological sample;
    (3) blocking proliferative capacity of T-cells in the biological sample and combining the sample T-cells with the antigen.

5. The method of claim 3, wherein the biological sample comprises peripheral blood mononuclear cells (PBMCs).

6. The method of claim 5, wherein antigen reactive T-cells are detected at concentrations less than about one to five T-cells per $10^5$ PBMCs.

7. The method of claim 1, wherein the T-cells are helper T-cells.

8. The method of claim 1, wherein the T-cells are reactive to an autoantigen.

9. The method of claim 1, wherein the soluble factor is a mammalian lymphokine and is selected from the group consisting of IFN-gamma, TNF-alpha and IL-2.

10. The method of claim 1, wherein a cytokine, growth factor or combination thereof, is added during or after step (a) to facilitate continued T-cell expansion.

11. The method of claim 1, wherein the antigen is an autoantigen of an autoimmune disease.

12. The method of claim 1, wherein the antigen is human myelin basic protein, a peptide derived therefrom, PPD, or tetanus toxoid.

13. The method of claim 11, wherein the autoimmune disease is multiple sclerosis.

14. The method of claim 11, wherein the autoantigen is myelin basic protein.

15. The method of claim 14, wherein the autoantigen is a peptide component of myelin basic protein.

16. The method of claim 15, wherein the peptide component is MBP 83–102.

17. The method of claim 1, wherein the solid support is a plastic support.

18. The method of claim 1, wherein the solid support comprises a first specific binding pair member for the soluble factor and the detecting step (d) further comprises:
   (1) binding a second specific binding pair member for the soluble factor to be assayed to the soluble factor captured in step (c) of claim 1;
   (2) binding a third specific binding pair member conjugated to a label wherein the third specific binding pair member is complementary to the second specific binding pair member; and
   (d) detecting the presence of the label.

19. The method of claim 18, wherein the first and second specific binding pair members are antibodies to the soluble factor, the third specific binding pair member is an antibody to the second specific binding pair member, and the label is an enzyme.

20. A method of periodically monitoring levels of antigen reactive T-cells in a patient comprising:
   (a) providing a sample of PBMCs from the patient;
   (b) freezing a portion of the sample of PBMCs to provide a control sample;
   (c) assaying the level of antigen reactive T-cells in the patient at periodic intervals using the assay of claim 1;
   (d) assaying the level of antigen reactive T-cells in a freshly thawed portion of the control sample using the assay of claim 1; and
   (e) comparing the levels observed in (c) and (d) to monitor the levels of antigen reactive T-cells in the patient.

21. A method of identifying an antigen which stimulates T-cells in a patient biological sample, said method comprising:
   (a) exposing the biological sample to a suspected antigen for a time period sufficient to permit T-cell expansion;
   (b) optionally, adding a cytokine(s) and/or growth factor (s) to facilitate continued T-cell expansion;
   (c) restimulating the T-cells with an effective amount of a combination of the antigen and antigen presenting cells for a second time period effective to induce secretion of a soluble factor;
   (d) detecting the presence of the soluble factor by capturing the soluble factor on a solid support; and
   (e) relating the presence of the soluble factor to be assayed to the ability of the antigen to stimulate the T-cells.

22. A method of identifying a patient having T-cells reactive to an autoantigen, said method comprising:
   (a) exposing a biological sample from the patient to the autoantigen for a time period sufficient to permit T-cell expansion;
   (b) optionally, adding a cytokine, growth factor or combination thereof, to facilitate continued T-cell expansion;
   (c) restimulating the T-cells with an effective amount of a combination of the antigen and antigen presenting cells for a second time period effective to induce secretion of a soluble factor;
   (d) detecting the presence of the soluble factor by capturing the soluble factor on a solid support; and
   (e) relating the presence of the soluble factor to the patient's reactivity to the autoantigen.

23. A method of screening for a putative drug capable of inducing deletion or inactivation of T-cells, said method comprising:
   (a) exposing a first portion of a biological sample to an antigen capable of stimulating T-cells and the putative drug for a time period sufficient to permit T-cell expansion and exposing a second portion of the biological sample to the antigen in the absence of the putative drug;
   (b) optionally; adding a cytokine, growth factor or a combination thereof, to facilitate continued T-cell expansion;
   (c) restimulating the T-cells with an effective amount of a combination of the antigen and antigen presenting cells for a second time period effective to induce secretion of a soluble factor;
   (d) quantitating the amount of the soluble factor by capturing the soluble factor on a solid support; and
   (e) relating the secretion of more soluble factor in the second portion compared to the first portion to the capability of the drug to induce deletion or inactivation in T-cells.

* * * * *